US009474640B2

(12) United States Patent
Johnson (10) Patent No.: US 9,474,640 B2
(45) Date of Patent: Oct. 25, 2016

(54) VESSEL BIFURCATION STENT DEPLOYMENT SYSTEM WITH ZIPPERED CATHETERS

(75) Inventor: Andrew K. Johnson, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 144 days.

(21) Appl. No.: 14/131,787

(22) PCT Filed: Jul. 12, 2012

(86) PCT No.: PCT/US2012/046457
§ 371 (c)(1),
(2), (4) Date: Jan. 9, 2014

(87) PCT Pub. No.: WO2013/009976
PCT Pub. Date: Jan. 17, 2013

(65) Prior Publication Data
US 2014/0148891 A1 May 29, 2014

Related U.S. Application Data

(60) Provisional application No. 61/506,713, filed on Jul. 12, 2011.

(51) Int. Cl.
*A61F 2/06* (2013.01)
*A61F 2/954* (2013.01)
(Continued)

(52) U.S. Cl.
CPC .............. *A61F 2/954* (2013.01); *A61F 2/97* (2013.01); *A61F 2/856* (2013.01); *A61F 2002/067* (2013.01); *A61F 2250/0001* (2013.01); *A61F 2250/0071* (2013.01)

(58) Field of Classification Search
CPC .... A61F 2/954; A61F 2/97; A61F 2002/067;
A61F 2/95; A61F 2/958; A61F 2/962;
A61F 2/966; A61F 2002/065; A61F
2002/9505; A61F 2002/9511; A61F
2002/9517; A61F 2002/9522; A61F
2002/9528; A61F 2002/9534; A61F
2002/9665
See application file for complete search history.

(56) References Cited

U.S. PATENT DOCUMENTS 5,755,771 A 5/1998 Penn et al.
6,059,779 A * 5/2000 Mills ................ A61B 17/12022
600/373

(Continued)

FOREIGN PATENT DOCUMENTS

EP 2036519 3/2009
EP 2552361 2/2013
(Continued)

OTHER PUBLICATIONS

Int'l Search Report and Written Opinion in App. No. PCT/US2012/046457 (2013).
(Continued)

*Primary Examiner* — Jonathan Miles
*Assistant Examiner* — Kankindi Rwego
(74) *Attorney, Agent, or Firm* — Barnes & Thornburg LLP; Alice O. Martin (57) ABSTRACT

A bifurcated catheter, which can deploy a bifurcated stent constructed as a single piece into a bifurcated vessel, is disclosed. The system may have two main parts—a y-shaped catheter with a splittable seam, and a custom made stent, which can be deployed with the bifurcated catheter. The disclosed bifurcated catheter permits a physician or operator to stent a vessel at a bifurcation of the vessel.

14 Claims, 10 Drawing Sheets

(51) Int. Cl.
*A61F 2/97* (2013.01)
*A61F 2/856* (2013.01)

(56) References Cited

U.S. PATENT DOCUMENTS

| | | | |
|---|---|---|---|
| 6,099,560 A | 8/2000 | Penn et al. | |
| 6,383,171 B1 * | 5/2002 | Gifford | A61F 2/07 604/508 |
| 6,409,750 B1 * | 6/2002 | Hyodoh et al. | 623/1.1 |
| 6,514,281 B1 * | 2/2003 | Blaeser | A61F 2/954 623/1.12 |
| 6,699,274 B2 * | 3/2004 | Stinson | A61F 2/90 606/108 |
| 7,169,177 B2 * | 1/2007 | Obara | 623/1.35 |
| 7,300,460 B2 * | 11/2007 | Levine | A61B 17/12022 623/1.35 |
| 8,562,566 B2 | 10/2013 | Weber et al. | |
| 2006/0190070 A1 | 8/2006 | Kieck et al. | |
| 2006/0293695 A1 * | 12/2006 | Ricci | A61F 2/958 606/108 |
| 2008/0188865 A1 * | 8/2008 | Miller | A61B 17/221 606/127 |
| 2009/0132019 A1 | 5/2009 | Duffy et al. | |

FOREIGN PATENT DOCUMENTS

| | | |
|---|---|---|
| JP | 08-280816 | 10/1996 |
| JP | 10-043313 | 2/1998 |
| JP | 2008-531187 | 2/2005 |
| WO | WO 96/14028 | 5/1996 |

OTHER PUBLICATIONS

Office Action issued in App. No. JP2014-520321 (Mar. 3, 2016).

* cited by examiner

VESSEL BIFURCATION STENT DEPLOYMENT SYSTEM WITH ZIPPERED CATHETERS

CROSS REFERENCE TO RELATED APPLICATIONS

This application is a U.S. nationalization under 35 U.S.C. §371 of International Application No. PCT/US2012/046457, filed Jul. 12, 2012, which claims the benefit of priority under 35 U.S.C. §119(e) to United States Provisional Patent Application No. 61/506,713, filed Jul. 12, 2011. The disclosures set forth in the referenced applications are incorporated herein by reference in their entireties.

BACKGROUND

1. Technical Field

This disclosure relates to medical devices and, more specifically, to medical devices for endovascular deployment in lumens of vasculatures of mammals.

2. Description of the Related Art

It is known that stents can be placed within the vasculature using endovascular techniques for the treatment of diseased vessels. Known applications of stents include treatment of stenotic and atherosclerotic lesions in the coronary, peripheral, and cerebral vasculature. Another common application of stents is the treatment of cerebral aneurysms. Stents are designed to oppose the subject's inner vascular walls and provide an unobstructed conduit for blood flow within the stent lumen.

Stents are generally designed as straight homogenous tubes using biocompatible materials designed to treat the vessel pathology. Placing stents into vessel bifurcations requires deployment of multiple stents given the materials currently available. When more than one device is placed with overlap, the risk of complication exponentially increases—vessel wall apposition is decreased and stent material extends into the vessel lumen more than single stent material. There are several stent designs to overcome the problems associated with a bifurcation, but no current design permits a unitary stent with three tubes to be placed into a bifurcating vessel and, due to the problems described above, such a unitary design is needed.

SUMMARY OF THE DISCLOSURE

A bifurcated catheter, which can deploy a bifurcated stent constructed as a single piece into a bifurcated vessel, is disclosed. The system may have two main parts: a y-shaped catheter with a splittable seam, and a custom made stent, which can be deployed with the novel catheter. The disclosed catheter provides an effective means for a physician or operator to stent a vessel at a bifurcation of that vessel.

The catheter may be composed of standard endovascular catheter materials; it may consist of a tubular body with hollow interior. The distal end that may be placed in the body may have two tubular sections or legs while the proximal end may include a single tubular section or single leg. Instead of meeting symmetrically at the intersection, one of the two legs at the distal end may slightly overlap the other leg at the distal end. The "inseam of the pants" may be connected in a way that permits the inseam to be split, allowing deployment of a bifurcated stent. The physician or operator may work at the proximal end of the catheter.

In one embodiment, the seam may be split by mechanical withdrawal of a thin filament holding the two edges of the catheter together at the inseam; the filament may course through the wall of the catheter so that it can be withdrawn by the operator through the proximal end of the catheter. In a second embodiment, the material connecting the two distal legs of the catheter may dissolve with application of electricity, so that electrical current applied through wires in the catheter can cause stepwise electrolysis to split the seam. In a third embodiment, a first compound can connect the two edges of the seam together, and a second compound causing a chemical reaction to dissolve the first compound can be applied through the catheter by the operator to split the seam. Or, the first compound may simply dissolve in bodily fluids. Other methods to split the seam between the two distal legs of the catheter not described herein would also apply to the same catheter design as full and to those skilled in the art.

The stent may be preloaded onto the distal end of a wire, which may be split into two legs at its distal end. The design fitting the stent to the wire may be similar to currently available stents; the stent may self-deploy when unsheathed from the catheter. However, the disclosed system may provide a bifurcated design of the wire, allowing advancement of the bifurcated stent in the catheter. Once the bifurcated catheter may be placed into the vessel bifurcation at a satisfactory position, the loaded stent and wires may be passed through the catheter so that one wire extends through each leg of the bifurcated catheter. The legs at the distal end of the wire may extend beyond the distal ends of the stent so that they may be navigated into the two ends of the catheter. Once the stent may be in the proper location, the seam of the bifurcated catheter may be split. As this happens, the distal ends of the stent may be unsheathed and deployed into the vessel. The legs of the distal end of the catheter may be disposed between the open stent and the wall of the vessel. After the distal ends of the stent are satisfactorily deployed, the catheter may be withdrawn unsheathing the remaining proximal leg or segment of the stent in fashion similar to currently available stent-deployment systems. The split legs of the catheter may be withdrawn during this maneuver as well.

The stent can be fitted with radiopaque markers to affirm proper positioning of the stent during and after deployment. The system may be utilized through a guide catheter. Prior to entry into the body, two standard endovascular wires may be passed through the bifurcated catheter with one passing into each distal leg at the intersection of the distal legs of the catheter. The bifurcated catheter may be advanced through the guide catheter. The wires may then be navigated individually into two distal branches of the vessel bifurcation. Once access to both branches may be achieved, the bifurcated catheter may be advanced until the crotch or intersection of the distal legs of the catheter rests on the bifurcation point of the vessel. The two wires may then be removed. The stent loaded on the stent-deploying wire may then be advanced into the catheter. The two distal legs of the wire may be passed into the two distal legs of the catheter, and again the crotch or intersection of the distal legs of the stent may be advanced to the crotch or intersection of the distal legs catheter. At this point, the catheter inseam may be separated using one of the aforementioned mechanisms. The catheter may be pulled in a proximal direction so that the stent may be unsheathed and deployed. The stepwise splitting of the inseam of the catheter may allow both legs to be pulled over the crotch or intersection of the distal legs of the stent keeping the intersection in place as the catheter may be withdrawn. The catheter may be pulled over the proximal end of the stent so that the stent may be fully deployed and essentially molded to the bifurcation of the vessel.

In one aspect, a deployment system for a bifurcated stent is disclosed. The deployment system includes a bifurcated catheter including a proximal first leg connected to a distal second leg and a distal third leg. The second and third legs including at least one splittable seam that extends across the second and third legs. The system further includes a first guide wire passing through the first and second legs of the bifurcated catheter and a second guide wire passing through the first and third legs of the bifurcated catheter. The first and second guide wires introduce the second and third legs of the bifurcated catheter into different but connected vessels. The system further includes a bifurcated stent-deployment guide wire including a third guide wire connected to a fourth guide wire and a fifth guide wire. The third, fourth and fifth guide wires are connected to a junction. The system further includes a bifurcated stent including a proximal first leg connected to a distal second leg and a distal third leg. The third guide wire may be received in the first leg of the bifurcated stent, the fourth guide wire may be received in the second leg of the bifurcated stent and the fifth guide wire may be received in the third leg of the bifurcated stent. The second leg of the bifurcated stent and the fourth guide wire are receivable in the second leg of the bifurcated catheter. The third leg of the bifurcated stent and the fifth guide wire are receivable into the third leg of the bifurcated catheter.

In another aspect, another deployment system for a stent is disclosed which includes a bifurcated catheter including a first leg connected to a second leg and a third leg at a first junction. The second and third legs include at least one splittable seam that extends across the second and third legs. The system further includes first and second guide wires for introducing the first, second and third legs of the bifurcated catheter into different but connected vessels. The system further includes a stent including a first leg connected to a second leg at a second junction. The system further includes a bifurcated stent-deployment guide wire with a third guide wire connected to a fourth guide and a fifth guide wire at a third junction. The third guide wire may be received in the first leg of the bifurcated stent and the fourth guide wire and first leg of the bifurcated stent may be receivable in the second leg of the bifurcated catheter. The fifth guide wire and the second leg of the bifurcated stent are receivable in the third leg of the bifurcated catheter.

In yet another aspect, a deployment system for a variable density stent is disclosed which includes a catheter comprising a second lumen comprising at least one splittable seam. The system further includes a first guide wire for introducing the catheter into a vascular system and a variable density stent.

Further, a method for installing a bifurcated stent into a bifurcated vessel of a vascular system is disclosed which includes: locating the bifurcated vessel in the vascular system, the bifurcated vessel including a first branch connected to a second branch and a third branch at a first junction and wherein the second and third branches are connected; introducing a first guide wire into the vascular system; introducing an introduction catheter over the first guide wire and into the vascular system; withdrawing the first guide wire; providing a bifurcated catheter including a proximal first leg connected to a distal second leg and a distal third leg at a second junction, the bifurcated catheter further including a splittable seam that extends along the second and third legs of the bifurcated catheter; providing a bifurcated stent including a proximal first leg connected to a distal second leg and a distal third leg at a third junction; providing a second guide wire that passes through the first and second legs of the bifurcated stent and a third guide wire that passes through the first and third legs of the bifurcated stent; inserting the bifurcated stent and second and third guide wires into the bifurcated catheter wherein the second leg of the bifurcated stent may be disposed in the second leg of the bifurcated catheter, the third leg of the bifurcated stent may be disposed in the third leg of the bifurcated catheter and the first leg of the bifurcated stent may be disposed in the first leg of the bifurcated catheter, and wherein the second guide wire passes through the first legs of the bifurcated catheter and bifurcated stent and through the second legs of the bifurcated catheter and bifurcated stent and the third guide wire passes through the first legs of the bifurcated catheter and bifurcated stent and through the third legs of the bifurcated catheter and bifurcated stent; inserting the bifurcated catheter, bifurcated stent, and second and third guide wires through the introduction catheter towards the bifurcated vessel and positioning the second legs of the bifurcated catheter and bifurcated stent and the second guide wire in the second branch of the bifurcated vessel and positioning the third legs of the bifurcated catheter and bifurcated stent and the third guide wire in the third branch of the bifurcated vessel; splitting the seam of the bifurcated catheter; withdrawing the bifurcated catheter; allowing the bifurcated stent to expand against interior surfaces of the first, second and third branches of the bifurcated vessel; and withdrawing the second and third guide wires.

In any one or more of the embodiments described above, the system may further include an introduction catheter and a sixth guide wire for introducing the introduction catheter into a vascular system. The bifurcated catheter and bifurcated stent may be capable of passing through the introduction catheter.

In any one or more the embodiments described above, the splittable seam may include an electrolytic material extending along the seam wherein the electrolytic material may be in communication with a power supply for splitting the splittable seam.

In any one or more the embodiments described above, the splittable seam may be split by exposure to a chemical.

In any one or more the embodiments described above, the splittable seam includes at least one chemical that, upon exposure to another chemical, dissolves and splits the splittable seam.

In any one or more the embodiments described above, the splittable seam may be coupled to a wire filament that, when pulled, breaks the splittable seam.

In any one or more the embodiments described above, the third junction may be disposed within the second junction and the second junction may be disposed within the first junction prior to splitting the seam of the bifurcated catheter and prior to withdrawing the second and third guide wires.

Other advantages and features may be apparent from the following detailed description when read in conjunction with the attached drawings.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale I and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1:
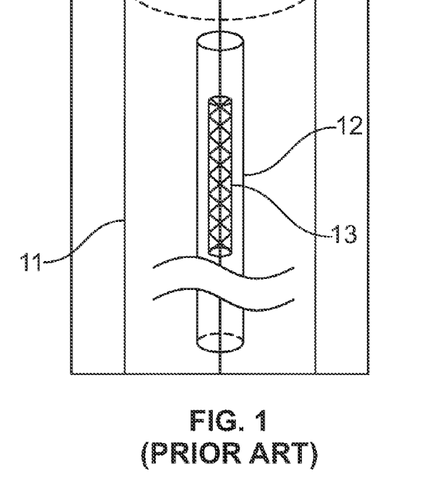
FIG. 1 shows a standard endovascular catheter with a standard endovascular self-deploying stent loaded on a wire (sheathed).
Figure 2:
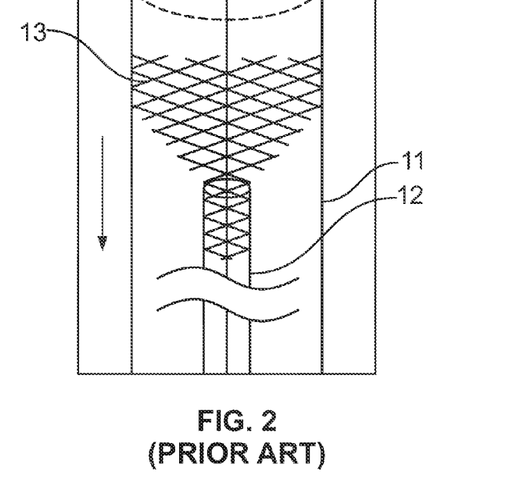
FIG. 2 shows a partially unsheathed standard endovascular stent. The direction of the arrow shows the catheter movement in the proximal direction, with the stent-deployment wire held in place as the stent is unsheathed.

A known introduction catheter or sheath 11, stent catheter 12 and stent 13 are shown in FIGS. 1-2. The self-expanding stent 13 may deploy automatically upon withdrawal of the catheter 12 as shown in FIG. 2.

The disclosed bifurcated stent deployment systems may include two main complements: an electrolytically-dividing bifurcated or y-shaped catheter for deploying a bifurcated or y-shaped guide wire and stent.

Figure 3:
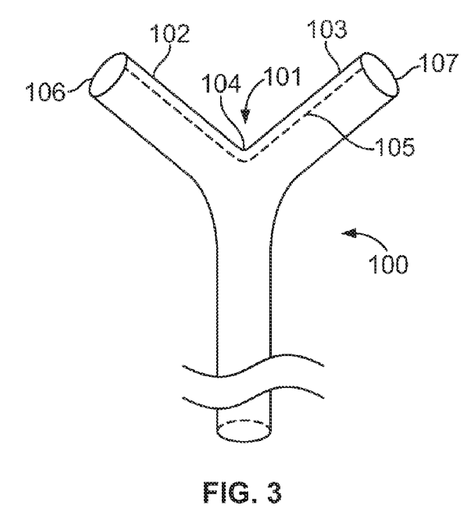
FIG. 3 shows a disclosed bifurcated endovascular catheter made with biocompatible material currently used in commercially available endovascular catheters. There may be a seam from one distal catheter leg to the other distal catheter leg.

Turning to FIG. 3, a disclosed bifurcated catheter 100 may fabricated from standard endovascular catheter materials. The distal end 101 may include two branches or legs 102, 103 at its junction 104. Instead of meeting symmetrically at the junction 104, one leg 102, 103 may slightly overlap the other leg 102, 103. The seam 105 that extends along the legs 102, 103 may be connected by filaments (not shown) that detach from each other with the application of electrical current, one or more chemicals or a mechanical force. When using current, the resistance from the current source to the filaments may progressively increase from the junction 104 toward the distal ends 106, 107 of the legs 102, 103 respectively. Thus, when electricity is supplied, separation at this seam 105 may start at the junction 104 and gradually split both legs 102, 103 until the legs 102, 103 are fully open at the seam 105. As an alternative, if an overlap is employed, the design of the overlap that is in place prior to splitting the seam 105 may allow the leg that overlaps initially to circumscribe the other leg so that when fully detached the two legs can fit into each other in a coaxial fashion creating a single tube.

Figure 4:
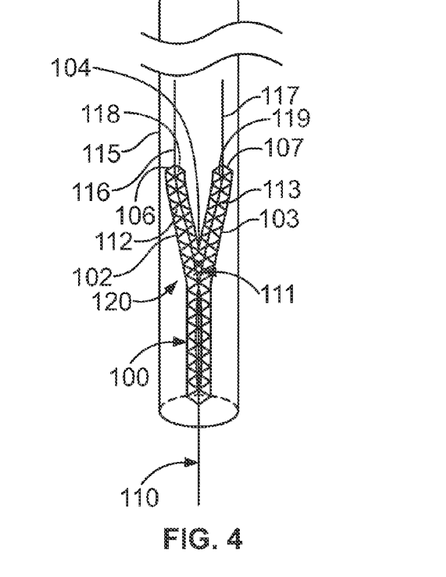
FIG. 4 shows a bifurcated stent loaded onto a bifurcated wire in similar fashion to that presented in FIG. 1.

Turning to FIG. 4, a stent-deploying y-shaped guide wire 110 may be fitted with a stent 111 having two legs 112, 113 and the stent 111 and guide wire 110 disposed within the bifurcated catheter 100 of FIG. 3. An introduction catheter is shown at 115. The branching of the stent 111 and the guide wire 110 may be in alignment thereby enabling the stent 111 to self-deploy when unsheathed from the bifurcated catheter 100 as shown in FIGS. 8-11. The stent 111 may self-deploy when unsheathed from the catheter 100. The distal legs 116, 117 of the wire 110 may extend beyond the distal ends 118, 119 of the stent 111 so that legs 116, 117 of the wire 110 may be navigated into the two distal ends 106, 107 ends of the bifurcated catheter 100.

Figure 5:
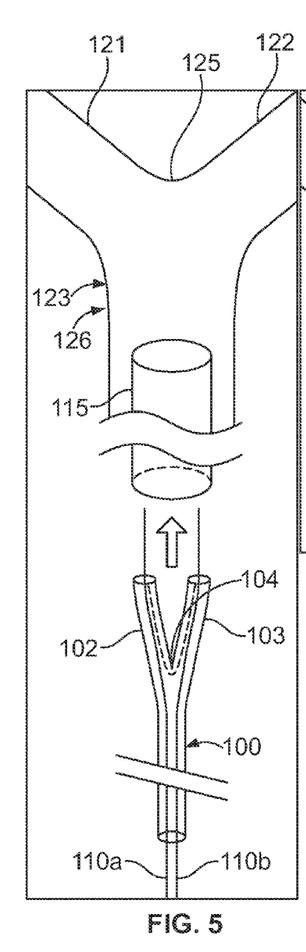
FIG. 5 shows a vessel bifurcation with a standard endovascular guide catheter introduced into the vessel proximal to the bifurcation. Two standard endovascular guide wires have been inserted into the disclosed bifurcated endovascular catheter shown in FIG. 3. The bifurcated catheter may be advanced into the guide catheter over the two guide wires.
Figure 6:
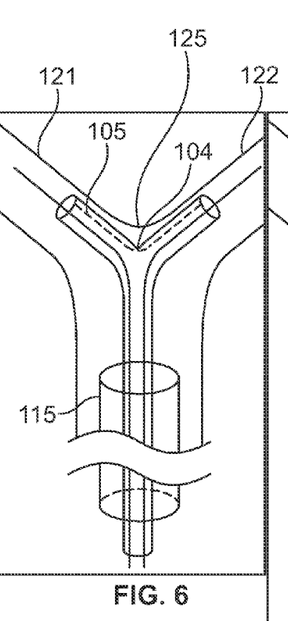
FIG. 6 shows the bifurcated catheter advanced over the guide wires and through the guide catheter until the intersection of the two distal legs of the catheter meets the bifurcation of the vessel.
Figure 7:
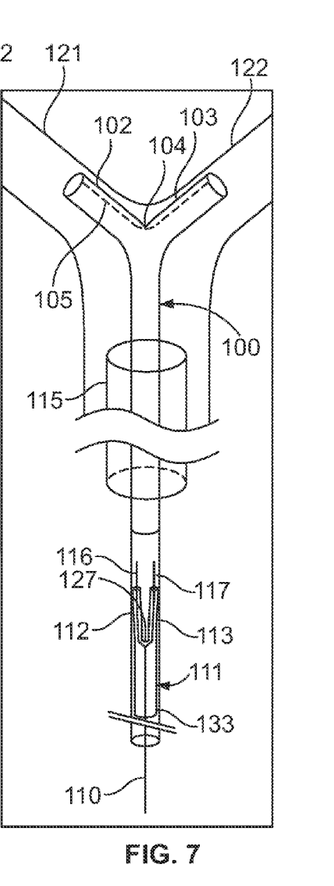
FIG. 7 shows the FIG. 6 after removal of the guide wires. The loaded stent of FIG. 4 has been inserted into the proximal end of the bifurcated catheter is ready to be inserted into the bifurcated catheter.
Figure 8:
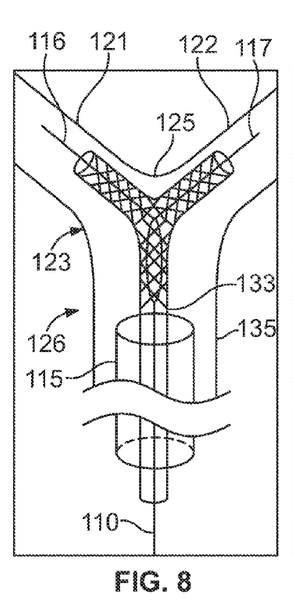
FIG. 8 shows the bifurcated stent, still loaded on the delivery guide wires advanced into the bifurcation of the vessel and bifurcated catheter. The bifurcated stent shown in FIG. 8 is ready for deployment.
Figure 9:
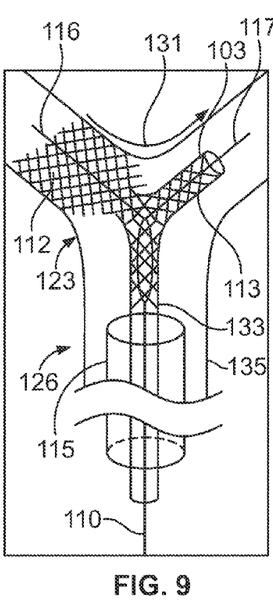
FIG. 9 shows part of the stent unsheathed by seam detachment of the bifurcated catheter. The arrow shows the direction of seam opening.
Figure 10:
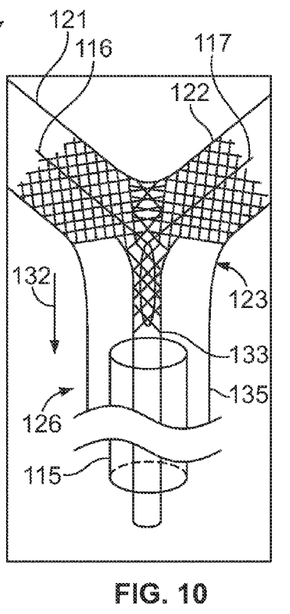
FIG. 10 shows the deployed section of stent after the seam is fully split. Only the proximal portion of the bifurcated stent is not deployed. The arrow shows the proximal direction of the catheter retrieval to unsheath the remaining portions of the stent and withdraw the opened distal legs of the bifurcated catheter into the guide catheter and out of the body.
Figure 11:
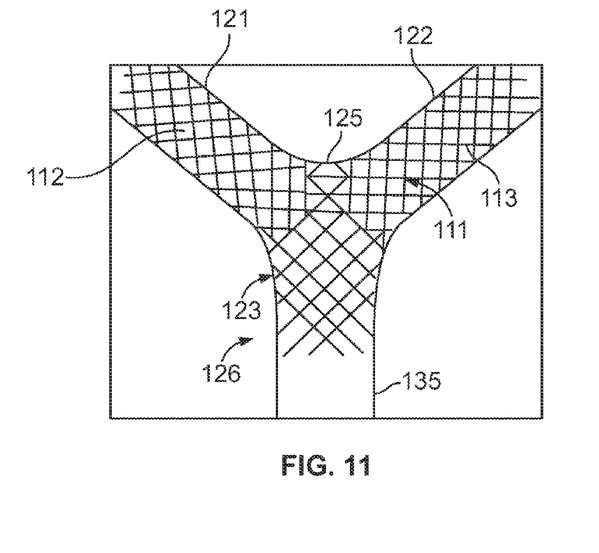
FIG. 11 shows a disclosed stent deployed in a vessel bifurcation after removal of wires and catheters.
Figure 13:
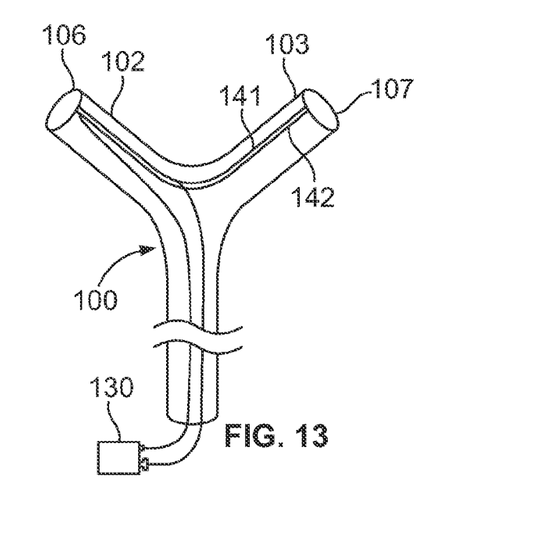
FIG. 13 shows an electrolytic splitting mechanism where the operator attaches direct current to two wires traversing inside the wall of the bifurcated catheter. The current causes sequential electrolysis of the seam based on increasing impedance from one end of the seam to the other. Alternating current could be used as well to take advantage of nonresistive impedance elements.

The system 120, which includes the wire 110, the bifurcated catheter 100 and the bifurcated stent 111 may be utilized through a introduction catheter 115. As an alternative shown in FIG. 5, prior to entry into the body, two standard endovascular wires 110a, 110b may be passed through the bifurcated catheter 100 with one wire 110a, 110b passing through each leg 102, 103 of the bifurcated catheter 100. The bifurcated catheter 100 may be advanced through the introduction catheter 115 over these two wires 110a, 110b. The wires 110a, 110b may then be navigated individually into two branches 121, 122 of the vessel bifurcation 123. Once access to both branches 121, 122 is achieved, the bifurcated catheter 100 may be advanced until the junction 104 of the bifurcated catheter 100 rests on the junction 125 of the vessel 126 is shown in FIG. 6. The two guidewires 110a, 110b may then be removed as shown in FIG. 7. The stent-deploying wire 110 may then be advanced into the catheter 100. The two legs 116, 117 may be passed into the two legs 102, 103 of the catheter 100 is shown in FIGS. 7-8, and the intersection 127 of the stent 111 and may be advanced towards the junction 104 of the catheter 100. At this point, the catheter 100 may be connected to an electrical current source 130 as shown in FIG. 13 for purposes of splitting the seam 105 that extends along the legs 102, 103 of the catheter 100 as shown in FIGS. 6-7. As shown in FIGS. 8-9, the seam 105 splits in the direction of the arrow 131 as the leg 112 of the stent 111 begins to deploy. As shown in FIG. 10, the catheter 100 may be pulled proximally or in the direction of the arrow 132 as it as the seam 105 splits and the stent 111 may be unsheathed from the catheter 100 and may be deployed at the bifurcation 123. The sequential electrolysis of the seam 105 of the catheter 100 may allow both legs 102, 103 of the catheter 100 to be pulled over the intersection 127 (FIG. 7) of the stent 111 keeping the intersection 127 of the stent 111 in place as the catheter 100 is withdrawn. The catheter 100 may be pulled over the proximal end 133 of the stent 111 so that the stent 111 may be fully deployed in a fashion molded to the bifurcation 123 of the vessel 126 as shown in FIG. 11.

The zippered catheter may have several available modifications including but not limited to those shown in in the drawings. For example, one leg 102, 103 of the catheter 100 may be small or removed allowing only a guide wire 110, 110a, 110b and not a stent 111 through the small leg 102, 103 which permits orientation of a non-branched stent (not shown). Further, the proximal stent portion 133 (FIG. 7) can be omitted allowing a stent to bridge across the branches 121, 122 of a bifurcation 123 was out stent material being disposed in the proximal or main portion 135 of the vessel 126. The catheter 100 can be unzipped from either end 106, 107 and not necessarily in the direction of the arrow 131 as shown in FIG. 9.

Figure 12:
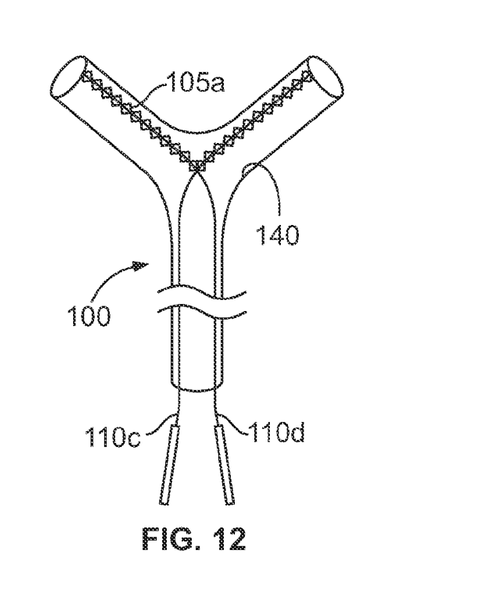
FIG. 12 shows a mechanical seam splitting mechanism where the operator pulls filaments that connect the two sides of the splittable seam. The filaments connect the operator to the distal end of the catheter through the wall of the bifurcated catheter.
Figure 14:
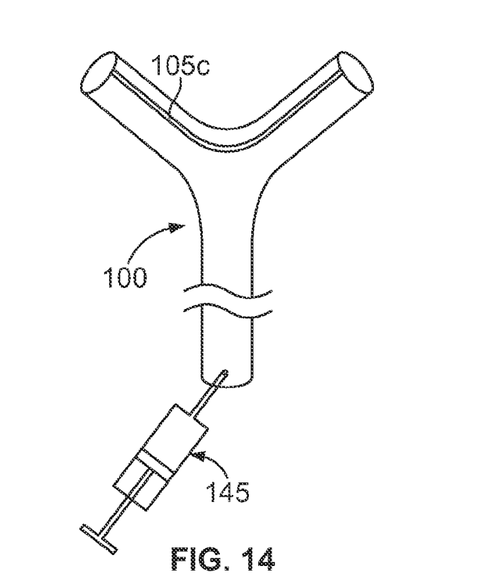
FIG. 14 shows a chemical mechanism where a first compound may be injected into the bifurcated catheter, which includes a seam. A second compound reacts with the first compound to dissolve the seam and release the two distal legs of the bifurcated catheter.
Figure 15:
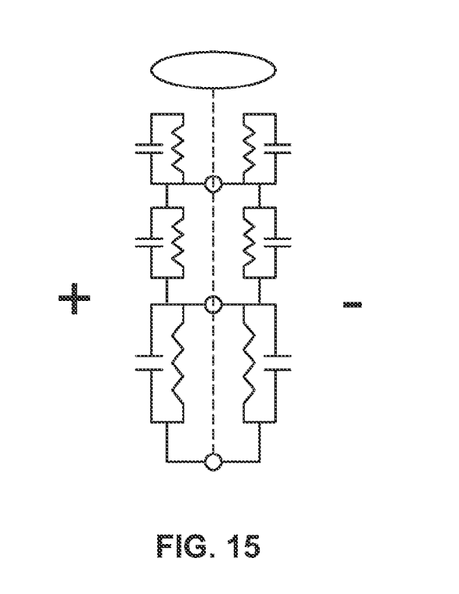
FIG. 15 illustrates the use of a circuit with variable impedance and units with distinct time constants allowing stepwise electrolysis to split the seam of a disclosed bifurcated catheter in the deployment of a disclosed bifurcated stent using variable-frequency alternating current.

Possible unzipping methods include but are not limited to electrolysis (FIGS. 13 and 15), mechanical (FIG. 12), and chemical mechanisms (FIG. 14). Possible electrolytic methods, similar to those deployed in electrolytically detachable coils or wires 141, 142 as shown in FIG. 13, and may further include gradient resistance from the one end 106 of one leg 102 to the other end 107 of the other leg 103 as shown in FIG. 13 with an electrical schematic shown in FIG. 15. Variable time constant impedances could also be used allowing tailored unzipping based on input electrical frequency. Mechanical unzipping from the distal end toward the proximal end could be based on guide wires 110c, 110d that are intrinsic to the catheter walls 140, which could be pulled releasing the mechanical bond holding the catheter seam 105a in place as shown in FIG. 12. FIG. 14 schematically illustrates the injection of one compound from an injection device 145 into the catheter 100 which includes a seam 105c coated with another compound that will be dissolved by the injected compound.

The available stents for use with zippered catheters 100 may be tailored to fit patient-specific anatomy is illustrated in FIGS. 39-44, 45-49, 50-53, 54-55, 56-59, and 60-67. The y-shaped system can be used for orientation of the stent 111 within the vessels 126, and the stent 111 can be engineered to create the desired specifications including curve and bifurcation shape, strut density, outward radial force, and length at all parts of both the normal vessels and the pathology. Potential pathologies include but are not limited to vessel stenoses, aneurysms, and thromboembolic lesions.

Figures 16, 17:
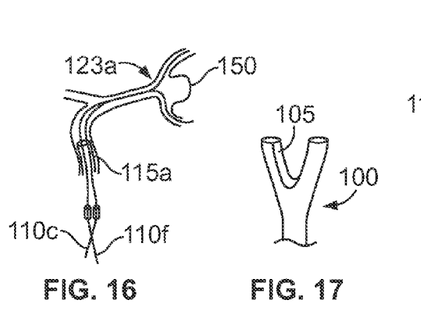
FIGS. 16-30 illustrate a sequential deployment of a disclosed bifurcated stent using a disclosed bifurcated catheter with a splittable seam and dual guide wires.
Figures 18, 19:
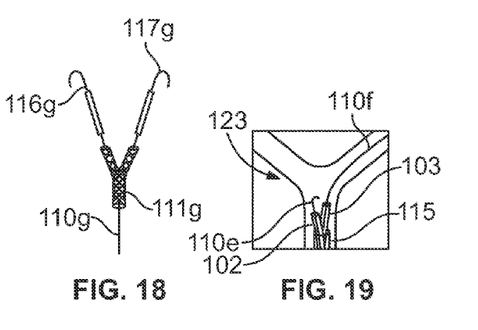
Figure 20:
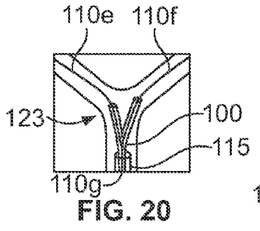
Figures 21, 22, 23:
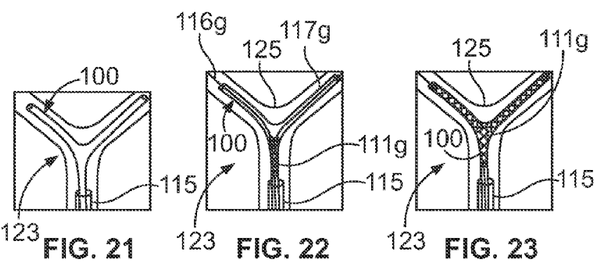
Figure 24:
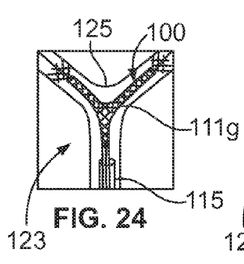
Figures 25, 26:
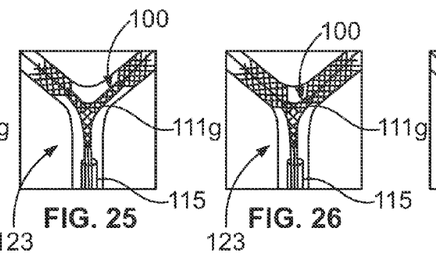
Figure 27:
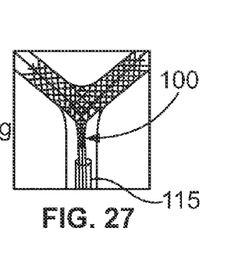
Figures 28, 29, 30:
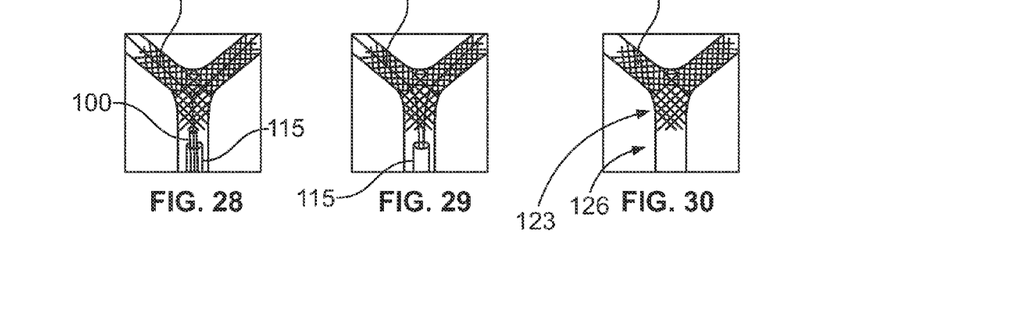

For example, FIG. 16 illustrates the use of the dual guide wires 110e, 110f being introduced through a guide catheter 115a into a vessel bifurcation 123 having an aneurysm 150. A bifurcated catheter 100 is shown in FIG. 17 with a seam 105. A bifurcated guide wire 110g having legs 116g, 117g with a bifurcated stent 111 mounted thereon is shown in FIG. 18. FIGS. 19-20 illustrate the introduction of the catheter 100 and guide wires 110e, 110f though a introduction catheter 115 into a vessel bifurcation 123. FIG. 21 illustrates the catheter 100 after the removal of the guide wires 110e, 110f. FIGS. 22-23 illustrate the introduction of the stent 111g and guide wires 116g, 117g through the introduction catheter 115 and into the bifurcated catheter 100. FIGS. 24-27 illustrate the splitting of the seam 105 (FIG. 17), which causes the deployment of the stent 111g (FIGS. 24-27). FIGS. 28-30 illustrate the withdrawal of the catheter 100 through the introduction catheter 115 (FIGS. 28-29) and the final position of the bifurcated stent 111g (FIGS. 30).

Figure 31:
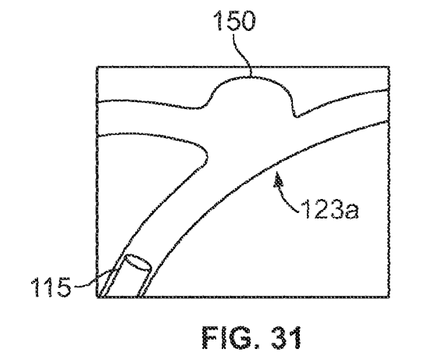
FIGS. 31-44 illustrate a sequential deployment of a disclosed bifurcated stent at a vessel bifurcation with an aneurysm using another disclosed bifurcated catheter with a splittable seam and dual guide wires and the introduction of an additional catheter through the proximal end of the stent for repairing the aneurysm.
Figure 32:
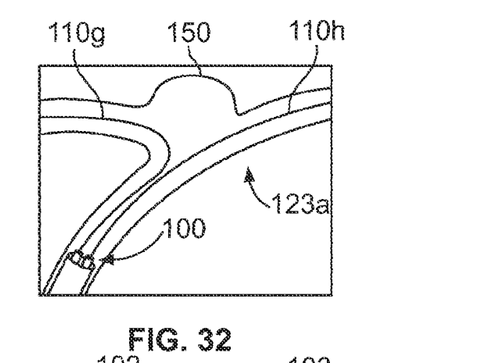
Figure 33:
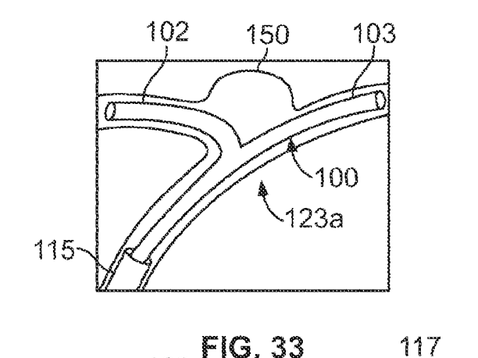
Figure 34:
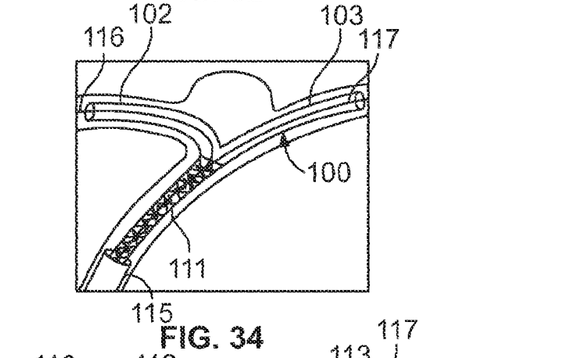
Figure 35:
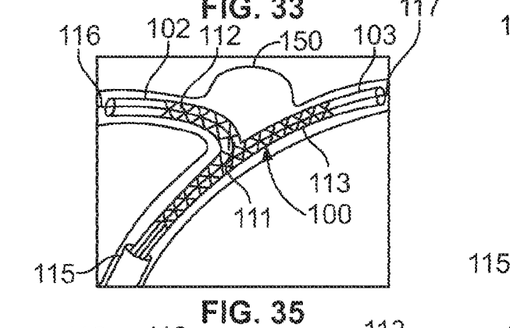
Figure 36:
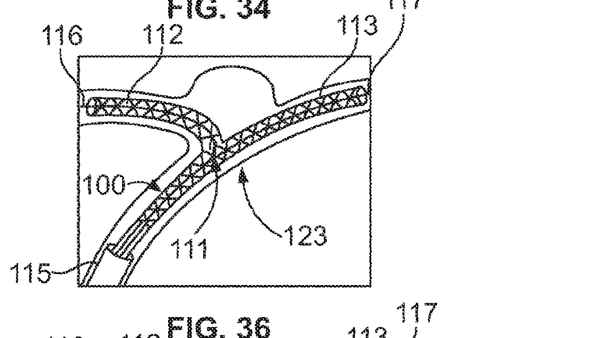
Figures 37, 38:
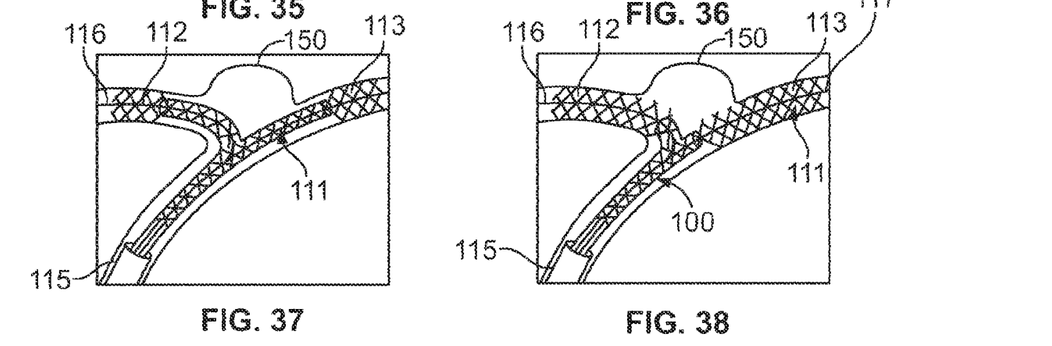
Figure 39:
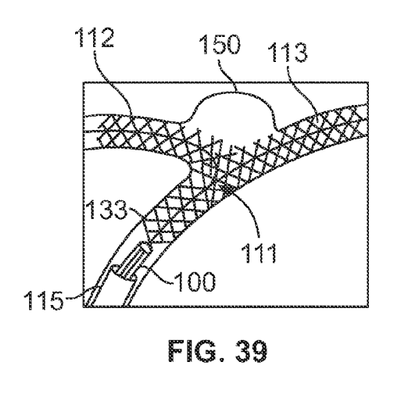
Figure 40:
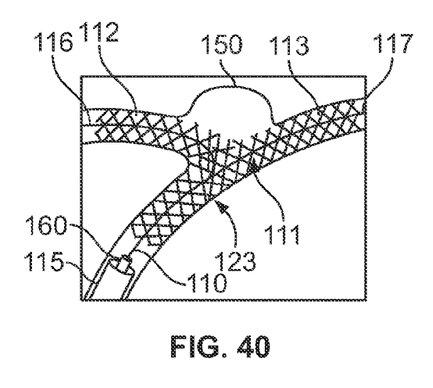
Figure 41:
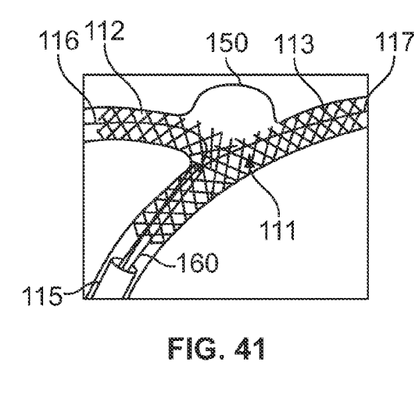
Figure 42:
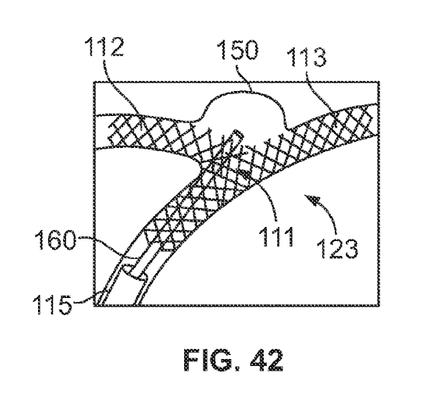
Figure 43:
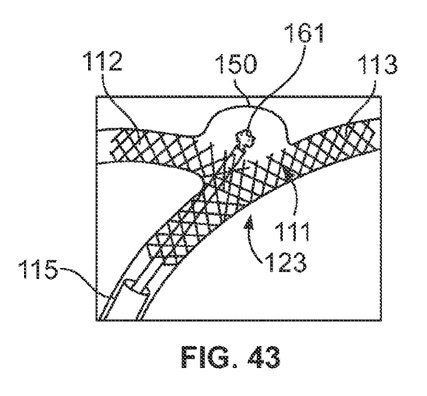
Figure 44:
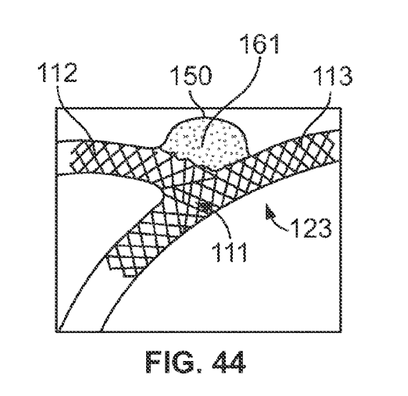
Figure 45:
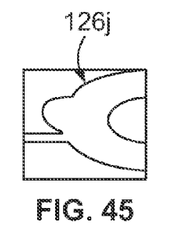
FIGS. 45-49 illustrate the use of an orientation guide wire to place a disclosed curved stent in a curved vessel in accordance with this disclosure.
Figure 46:
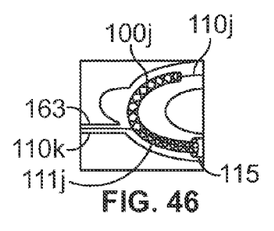

FIGS. 31-44 illustrates the deployment of a bifurcated catheter 100 and a bifurcated stent 111 across a vessel bifurcation 123a with an aneurysm 150. The introduction catheter 115 is shown in FIG. 31. The introduction of the bifurcated catheter 100 and guide wires 110g, 110h is shown in FIG. 32. The deployment of the bifurcated catheter 100 after the guide wires 110g, 110h have been withdrawn is shown in FIG. 33 the introduction of a bifurcated stent 111 that may be been mounted on a bifurcated guide wire 110 with legs 116, 117 into the bifurcated catheter 100 is shown in FIGS. 34-36. The reader will note that the bifurcated guide wire 110 may be replaced with a pair of guide wires. FIGS. 37-39 illustrate the unzipping or the cleavage of the seam 105 (not shown in FIGS. 31-44) and the deployment of the legs 112, 113 of the stent 111 (FIGS. 37-38) as well as the deployment of the proximal end 133 of the stent 111 (FIG. 39). FIG. 39 also illustrates the withdrawal of the catheter 100 while leaving the guide wire 110 and guide wire legs 116, 117 in place. As shown in FIGS. 39-42, the introduction catheter 115 may also be used for inserting an additional catheter 160 over the guide wire 110. In FIGS. 41-42, the guide wire 110 may be withdrawn through the additional catheter 160 and FIGS. 43-44 illustrate how the additional catheter 160 may be used to inject medicine or repair material 161 into the aneurysm 150 while the stent 111 remains deployed in the vessel bifurcation 123.

Figure 47:
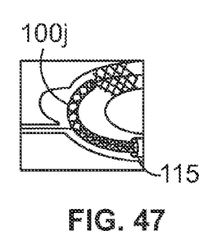
Figure 48:
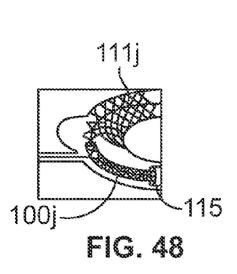
Figure 49:
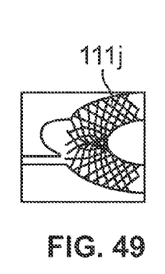
Figure 50:
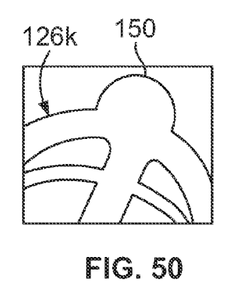
FIGS. 50-53 illustrate the deployment of a disclosed "bridge" stent across an upper section of a T-shaped vessel junction with an aneurysm.

FIGS. 45-49 illustrate the deployment of a curved stent 111j into a curved vessel 126j. An introduction sheath or catheter 115 is employed with a curved catheter 100j which may be equipped with curved guide wire 110j and an orientation guide wire 110k that may be inserted into a branch 163 of the curved vessel 126j. The curved catheter 110j may be equipped with a seam 105 (not shown in FIGS. 45-49) that may be split as shown in FIGS. 47-48 before the guide wire 110j an orientation guide wire 110k are withdrawn. The deployed curved stent 111j is shown in FIG. 49.

FIGS. 50-53 illustrate the deployment of a bridge stent 111m in a curved vessel 126k with an aneurysm 150. A bifurcated or T-shaped catheter 100m may be introduced through the introduction catheter 115 which may or may not be preloaded with a bridge stent 111m. The catheter 100m may be split using one of the techniques discussed above to provide a deployed bridge stent 111m across the aneurysm 150 which may or may not be filled with repair material or medicine 161.

Figure 54:
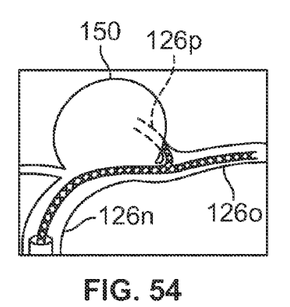
FIGS. 54-55 illustrate the deployment of a disclosed variable density stent across an aneurysm at a vessel junction accordance with this disclosure, where the struts of the stent covering the aneurysm may be more tightly packed.
Figure 55:
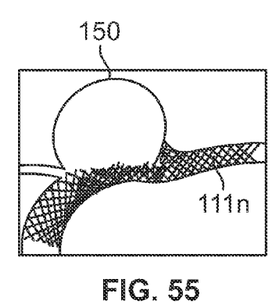
Figure 56:
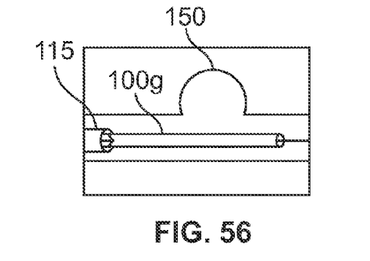
FIGS. 56-59 illustrate the deployment of a stent across an aneurysm using a zippered catheter in accordance with this disclosure.

FIGS. 54-55 illustrate the deployment of a stent 111n across an aneurysm 150 that has a variable density. Specifically, the stent 111n may be more dense at the aneurysm 150 and less dense along the branches 126n, 126o. The smaller branch 126p may be used for orientation purposes.

Figure 57:
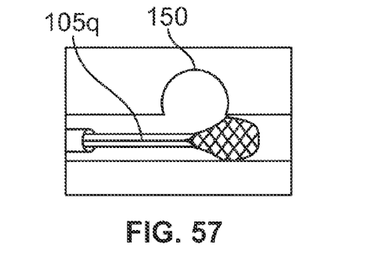
Figure 58:
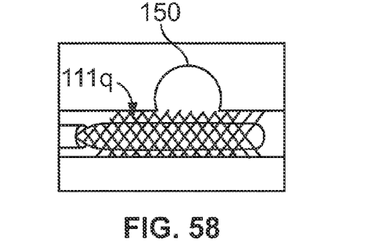
Figure 59:
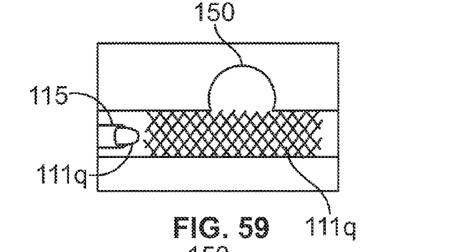
Figure 60:
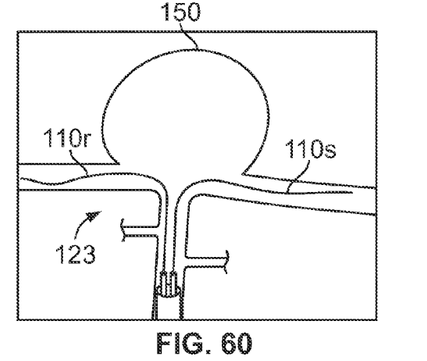
FIGS. 60-67 illustrate another sequential deployment of a disclosed bifurcated stent using another disclosed splittable catheter with separately split legs and dual guide wires.
Figure 61:
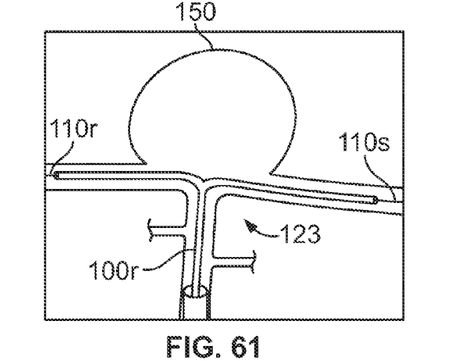
Figure 62:
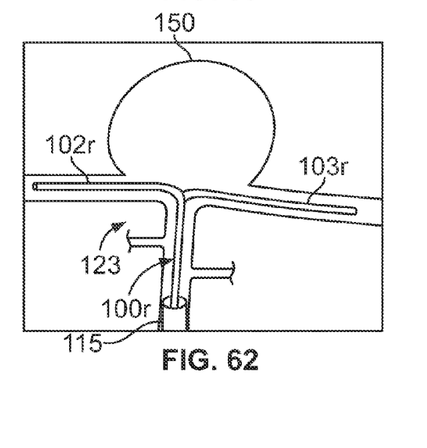

FIGS. 56-59 illustrate the deployment of a straight stent 111q across an aneurysm 150. A catheter 100q may be introduced through an introduction catheter 115 (FIG. 56) and may include a seam 105q that can be split as shown in FIGS. 57-58 to the employee the stent 111q across the aneurysm 150 while the split catheter 111q may be withdrawn through the introduction catheter 115 as shown in FIGS. 58-59.

Figure 51:
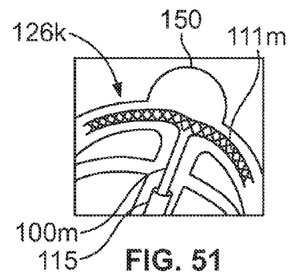
Figure 52:
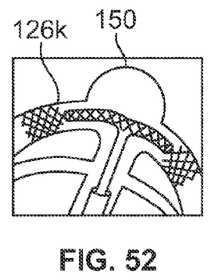
Figure 53:
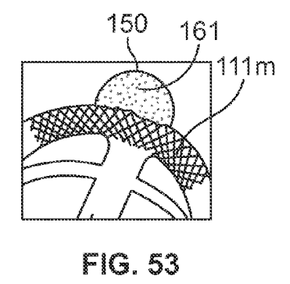
Figure 63:
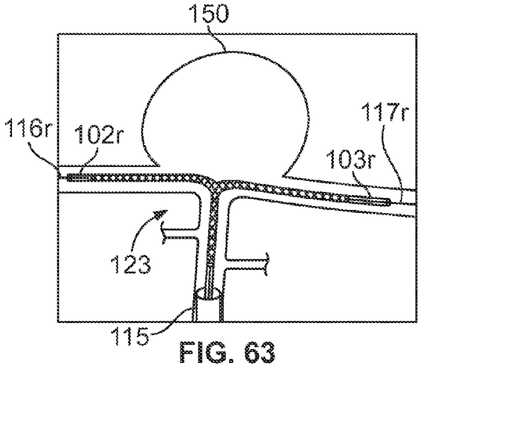
Figure 64:
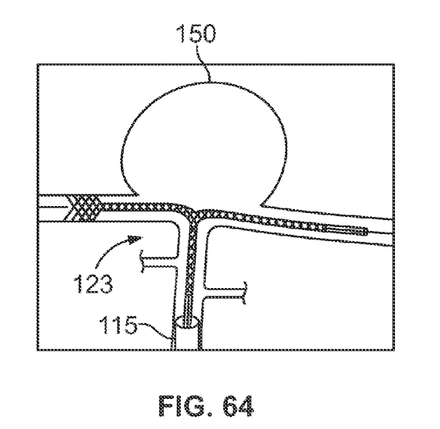
Figure 65:
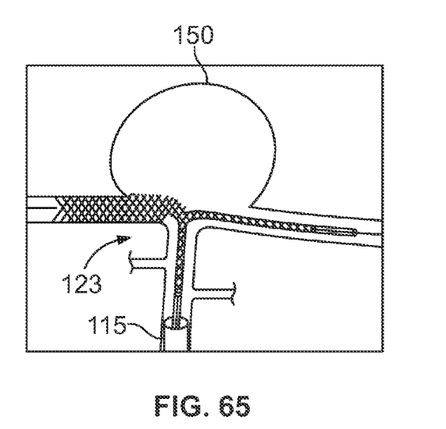
Figure 66:
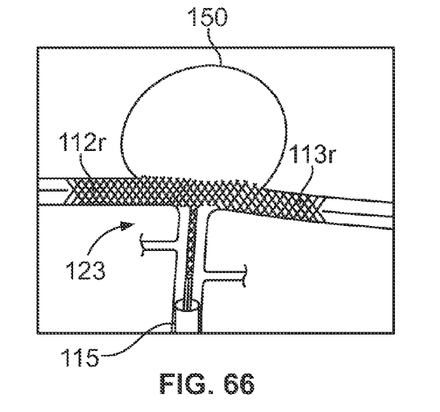
Figure 67:
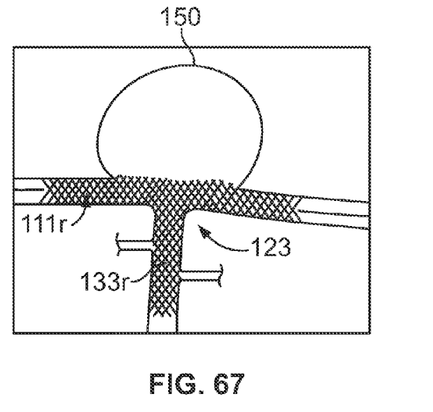

FIGS. 60-67 illustrate a customized stent 111r that may be deployed using a bifurcated catheter 100r and one or two guide wires shown at 110r, 110s. The stent 111r may or may not be preloaded into the catheter 100r as shown in FIGS. 63. As shown in FIGS. 62-66, the legs 102r, 103r may be split or unzipped sequentially or simultaneously before the bifurcated catheter 100r and guide wires 116r, 117r are withdrawn through the introduction catheter 115. In the embodiment shown in FIGS. 60-67, a bifurcated stent 111r is shown with a pair of outwardly extending legs 112r, 113r and a proximal leg 133r. However, the system shown in FIGS. 60-67 may also be used to install a bridge stent as shown in FIGS. 51-53.

INDUSTRIAL APPLICABILITY

Stent use has become prevalent in the treatment of cerebrovascular, cardiovascular, and other vascular diseases. Stents are used to treat stenosis of arteries, and they can be used to treat aneurysms. These pathologies are very common at vessel bifurcation points and present a challenge to endovascular therapy. Current techniques include stenting the parent vessel and main branch only, which may incompletely treat a lesion or placing stents in a y-fashion such that the stents overlap in the parent vessel and one stent is deployed through the interstices of the other stent. The latter technique may decrease wall apposition of the stents and leave stent struts in the lumen of the vessels, both of which decrease the chances of endothelialization of the stent surfaces and increase the risk of thromboembolic complications.

Patients who receive stents are routinely treated with anti-platelet therapy to prevent thromboembolic complications; however, these medications carry risks including bleeding. It is thought that endothelialization of the stent eventually reduces or eliminates the requirement of anti-platelet therapy.

The proposed bifurcation stent would increase vessel wall apposition and reconstruct vessel bifurcations to maximize luminal diameter, thus increasing endothelialization and minimizing stenosis, respectively. Currently there is no way to orient a tailored stent or place a single stent against all walls of a bifurcation. The proposed delivery systems provide novel ways to deploy a tailored stents through a single guide catheter.

Treatment of cerebrovascular, cardiovascular, and peripheral vascular diseases carries a large market share in health care, and endovascular treatments and devices are extraordinarily profitable. The bifurcated catheter and stent deployment system optimizes vessel reconstruction solving a difficult and very common problem.

Currently, there are a discrete number of stents available various diameters, lengths, and outward radial force. A key commercial aspect of the disclosed deployment systems would be the creation of anatomically exact stents tailored to a patient's unique vessel features and pathology. Patients may have a three-dimensional diagnostic angiogram, and then the images could be used by the manufacturer to design a stent that fits the bifurcation in question. The stent could then be deployed with proper orientation using the described catheter system to maximize treatment of lesions and minimize stent-associated risk to the patient.

The zippered bifurcated catheter permits placement of y-shaped stents that previously did not have an acceptable method of deployment. The zippered catheter may have applications beyond bifurcation stenting.

Variations include changes in the angle of the bifurcated catheter and stent. A stent could be deployed without a parent artery component with the system, stenting from one daughter vessel to the other; this would be ideal for T-shaped bifurcations. Stent deployment wires could be constructed with nonbranching stent, using the second catheter branch to anchor the stent or hold open a vessel during stent deployment with a balloon. Variations of the stent shape, structure, size, and radial force are innumerable.

While only certain embodiments have been set forth, alternatives and modifications may be apparent from the above description to those skilled in the art. These and other alternatives are considered equivalents and within the spirit and scope of this disclosure and the appended claims.

The invention claimed is:

1. A deployment system for a bifurcated stent, the system comprising:
   a bifurcated catheter comprising a proximal first leg connected to a distal second leg and a distal third leg, the second and third legs including at least one splittable seam that extends across the second and third legs,
   a first guide wire passing through the first and second legs of the bifurcated catheter and a second guide wire passing through the first and third legs of the bifurcated catheter, the first and second guide wires for introducing the second and third legs of the bifurcated catheter into different but connected vessels, the first and second guide wire configured to assist with navigating the second and third legs of the bifurcated catheter in the vessels,
   a third guide wire that is a bifurcated stent-deployment guide wire, the bifurcated stent-deployment guide wire including a proximal first leg connected to a distal second leg and a distal third leg at a junction, a bifurcated stent comprising a proximal first leg connected to a distal second leg and a distal third leg, the proximal first leg of the bifurcated stent-deployment guide wire being received in the first leg of the bifurcated stent, the distal second leg of the bifurcated stent-deployment guide wire being received in the second leg of the bifurcated stent, and the distal third leg of the bifurcated stent-deployment guide wire being received in the third leg of the bifurcated stent, the second leg of the bifurcated stent and the distal second leg of the bifurcated stent-deployment guide wire being receivable into the second leg of the bifurcated catheter, the third leg of the bifurcated stent and the distal third leg of the bifurcated stent-deployment guide wire being receivable into the third leg of the bifurcated catheter.

2. The deployment system of claim 1 further including an introduction catheter and a fourth guide wire for introducing the introduction catheter into a vascular system, the bifurcated catheter and bifurcated stent being capable of passing through the introduction catheter.

3. The deployment system of claim 1 wherein the splittable seam comprises an electrolytic material extending along the seam, the electrolytic material being in communication with a power supply for splitting the splittable seam.

4. The deployment system of claim 1 wherein the splittable seam may be split by exposure to a chemical.

5. The deployment system of claim 1 wherein the splittable seam includes at least one chemical that, upon exposure to another chemical, dissolves and splits the splittable seam.

6. The deployment system of claim 1 wherein the splittable seam is coupled to a wire filament that, when pulled, breaks the splittable seam.

7. The deployment system of claim 1 wherein the splittable seam is coupled to a wire filament that, when pulled, breaks the splittable seam.

8. A deployment system for a bifurcated stent, the system comprising:

a bifurcated catheter comprising a first leg connected to a second leg and a third leg at a first junction, the second and third legs including at least one splittable seam that extends across the second and third legs, first and second guide wires for introducing the first, second and third legs of the bifurcated catheter into different but connected vessels, the guide wires configured to guide the first, second and third legs of the bifurcated catheter in the vessels, a bifurcated stent comprising a first leg connected to a second leg at a second junction, a third guide wire that is a bifurcated stent-deployment guide wire, the bifurcated stent-deployment guide wire comprising a proximal first leg connected to a distal second leg and a distal third leg, the proximal first leg of the stent-deployment guide wire being received in the first leg of the bifurcated stent, the distal second leg of the bifurcated stent-deployment guide wire and the first leg of the bifurcated stent being receivable in the second leg of the bifurcated catheter, the fifth distal third leg of the bifurcated stent-deployment guide wire being received in the second leg of the bifurcated stent, the distal third leg of the bifurcated stent-deployment guide wire and the second leg of the bifurcated stent being receivable in the third leg of the bifurcated catheter.

9. The deployment system of claim 8 further including an introduction catheter and a fourth guide wire for introducing the introduction catheter into a vascular system, the bifurcated catheter and bifurcated stent being capable of passing through the introduction catheter.

10. The deployment system of claim 8 wherein the splittable seam comprises an electrolytic material extending along the seam, the electrolytic material being in communication with a power supply for splitting the splittable seam.

11. The deployment system of claim 8 wherein the splittable seam may be split by exposure to a chemical.

12. The deployment system of claim 8 wherein the splittable seam includes at least one chemical that, upon exposure to another chemical, dissolves and splits the splittable seam.

13. A method for installing a bifurcated stent into a bifurcated vessel of a vascular system, the method comprising:

locating the bifurcated vessel in the vascular system, the bifurcated vessel including a first branch connected to a second branch and a third branch at a first junction and wherein the second and third branches are connected, introducing a first guide wire into the vascular system, introducing an introduction catheter over the first guide wire and into the vascular system, withdrawing the first guide wire, providing a bifurcated catheter including a proximal first leg connected to a distal second leg and a distal third leg at a second junction, the bifurcated catheter further including a splittable seam that extends along the second and third legs of the bifurcated catheter, providing a bifurcated stent including a proximal first leg connected to a distal second leg and a distal third leg at a third junction, providing a second guide wire that passes through the first and second legs of the bifurcated stent and a third guide wire that passes through the first and third legs of the bifurcated stent, inserting the bifurcated stent and second and third guide wires into the bifurcated catheter wherein the second leg of the bifurcated stent is disposed in the second leg of the bifurcated catheter, the third leg of the bifurcated stent is disposed in the third leg of the bifurcated catheter and the first leg of the bifurcated stent is disposed in the first leg of the bifurcated catheter, and wherein the second guide wire passes through the first legs of the bifurcated catheter and bifurcated stent and through the second legs of the bifurcated catheter and bifurcated stent and the third guide wire passes through the first legs of the bifurcated catheter and bifurcated stent and through the third legs of the bifurcated catheter and bifurcated stent, inserting the bifurcated catheter, bifurcated stent, and second and third guide wires through the introduction catheter towards the bifurcated vessel and positioning the second legs of the bifurcated catheter and bifurcated stent and the second guide wire in the second branch of the bifurcated vessel and positioning the third legs of the bifurcated catheter and bifurcated stent and the third guide wire in the third branch of the bifurcated vessel, splitting the seam of the bifurcated catheter, withdrawing the bifurcated catheter, allowing the bifurcated stent to expand against interior surfaces of the first, second and third branches of the bifurcated vessel, and withdrawing the second and third guide wires.

14. The method of claim 13 wherein the third junction is disposed within the second junction and the second junction is disposed within the first junction prior to splitting the seam of the bifurcated catheter and prior to withdrawing the second and third guide wires.

\* \* \* \* \*